United States Patent
Doerr et al.

(10) Patent No.: US 8,423,133 B2
(45) Date of Patent: Apr. 16, 2013

(54) SWITCHED PROTECTIVE DEVICE AGAINST ELECTROMAGNETIC INTERFERENCE

(75) Inventors: Thomas Doerr, Berlin (DE); Ingo Weiss, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 232 days.

(21) Appl. No.: 12/970,748

(22) Filed: Dec. 16, 2010

(65) Prior Publication Data

US 2011/0152972 A1 Jun. 23, 2011

Related U.S. Application Data

(60) Provisional application No. 61/288,857, filed on Dec. 22, 2009.

(51) Int. Cl.
*A61N 1/16* (2006.01)
(52) U.S. Cl.
USPC .................................. 607/2; 607/37; 607/63
(58) Field of Classification Search .................. 607/2, 5, 607/9, 36, 37, 63
See application file for complete search history.

(56) References Cited

U.S. PATENT DOCUMENTS

| | | | |
|---|---|---|---|
| 5,817,136 A | 10/1998 | Nappholz et al. | |
| 5,968,083 A | 10/1999 | Ciciarelli et al. | |
| 6,198,972 B1 * | 3/2001 | Hartlaub et al. | 607/63 |
| 6,901,292 B2 | 5/2005 | Hrdlicka et al. | |
| 7,164,950 B2 * | 1/2007 | Kroll et al. | 607/36 |
| 7,450,996 B2 | 11/2008 | MacDonald et al. | |
| 7,561,915 B1 * | 7/2009 | Cooke et al. | 607/31 |
| 7,729,770 B2 * | 6/2010 | Cabelka et al. | 607/37 |
| 8,032,228 B2 * | 10/2011 | Ameri et al. | 607/62 |
| 2002/0038135 A1 * | 3/2002 | Connelly et al. | 607/32 |
| 2002/0133204 A1 | 9/2002 | Hrdlicka et al. | |
| 2003/0083726 A1 * | 5/2003 | Zeijlemaker et al. | 607/122 |
| 2004/0263173 A1 * | 12/2004 | Gray | 324/322 |
| 2005/0090886 A1 | 4/2005 | MacDonal et al. | |
| 2005/0197677 A1 * | 9/2005 | Stevenson | 607/36 |
| 2008/0154342 A1 | 6/2008 | Digby et al. | |

OTHER PUBLICATIONS

European Search Report dated May 3, 2011 (5 pages).

* cited by examiner

*Primary Examiner* — Carl H Layno
*Assistant Examiner* — Eugene Wu
(74) *Attorney, Agent, or Firm* — ARC IP Law, PC; Joseph J. Mayo (57) ABSTRACT

A device and a method for working in the presence of electromagnetic fields, in particular fields occurring in magnetic resonance tomography (referred to below as "MRT" or "MRI") imaging devices. More precisely, the invention relates to a medical device (MD) in which an electrode is in contact with bodily tissue, and for detection of electromagnetic interference fields the input characteristic of the MD is automatically modified by a switching device in such a way that the influences of the electromagnetic interference fields are minimized.

13 Claims, 8 Drawing Sheets

SWITCHED PROTECTIVE DEVICE AGAINST ELECTROMAGNETIC INTERFERENCE

This application claims the benefit of U.S. Provisional Patent Application 61/288,857, filed on Dec. 22, 2009, which is hereby incorporated herein by reference.

BACKGROUND OF THE INVENTION

1. Field of the Invention

Embodiments of the invention relate to a device and a method for working in the presence of electromagnetic fields, in particular fields occurring in magnetic resonance tomography imaging devices. ("MRT" or "MRI" stand for magnetic resonance tomography and magnetic resonance imaging respectively, wherein these two acronyms are used interchangeably herein).

2. Description of the Related Art

Although MRI testing is becoming increasingly important in diagnostic medicine, it is contraindicated for some patients. Such contraindication may result from an active implanted medical device (also referred to below as "implant" or "IMD"). Besides MRI testing, however, other technical applications pose a risk to the user of medical devices or implantable medical devices, particularly when such applications generate strong electromagnetic interference fields (electromagnetic interference (EMI)) in their surroundings.

In order to still allow MRI testing or working in the surroundings of electromagnetic interference fields, various approaches are known which relate either to performing the MRI testing or to the implantable medical device.

Among others, technologies based on conventional processes for identifying magnetic fields are known for detecting magnetic fields. US 2008/0154342 describes a method which uses a giant magnetoresistance (GMR) sensor to detect problematic magnetic fields from MRT devices. However, these technological approaches are not very specific, and create increased energy requirements which result in a shorter operating period for equivalent energy reserves.

A further technological approach is the use of optical signal transmission instead of typical electrode lines based on electrical signal transmission. Use of these optical lines prevents the injection of electromagnetic interference fields from an MRI device into the electrode lines, but the overall system is more complex since on the one hand the electrical signals must first be converted to optical signals, and on the basis of the signals the stimulation pulses must be generated from the optical signals at the stimulation site, and on the other hand signals that are measured at the stimulation site must likewise be converted. As a rule, such higher-complexity systems also increase the energy requirements for an implant. Such a system based on optical signal transmission is described in US 2005/0090886 and U.S. Pat. No. 7,450,996.

In addition, a system is known from US 2002/0133204 and U.S. Pat. No. 6,901,292 which by selection of certain protective devices provides various modes for operating an electrical implant. A disadvantage of this system is that for high RF fields it also allows heating of the electrodes, since the focus of the cited documents is on electromagnetic compatibility with metal detectors and electronic security units.

BRIEF SUMMARY OF THE INVENTION

The object of one or more embodiments of the invention is to provide a device and a method for medical devices and implantable medical devices which eliminate the disadvantages of the prior art and allow safe operation in the presence of electromagnetic interference fields. The object is achieved by use of a medical device (MD) having the features as claimed herein.

The medical device (MD) comprises a unit for detecting electromagnetic interference, having at least one sensor and/or indicator for electromagnetic interference fields and a switching device, at least one electrode, at least one control unit which is connected or connectable to the unit for detecting electromagnetic interference, and at least one detection unit and/or at least one stimulation unit which are respectively connected or connectable to the at least one control unit and the at least one electrode, the at least one electrode being in contact with bodily tissue, and for detection of electromagnetic interference fields by the unit for detecting electromagnetic interference the input characteristic of the at least one electrode for the electronics system of the MD or IMD is automatically modified by means of the at least one switching device in such a way that the influences of the electromagnetic interference fields are minimized.

For example, the input characteristic is modified using at least one EMI capacitor and/or a resonant circuit and/or other suitable components. An EMI capacitor is a capacitor for reducing the influences of electromagnetic interference radiation. The unit for detecting electromagnetic interference may be composed of a sensor and/or indicator for electromagnetic fields and/or a combination of multiple sensors and/or indicators for electromagnetic fields. Examples of such sensors and indicators, without being limited thereto, include GMR sensors, MagFET sensors, Hall sensors, electro-optical converters, monitoring of battery voltages during capacitor charging processes, detection of RF fields, detection of magnetic gradient fields, detection of currents induced by electromagnetic fields, and detection of specific vibrations, or components designed as sensors for detection of vibrations induced by Lorentz forces.

The MD is preferably an implantable medical device (IMD).

It is also preferred that the at least one electrode is situated in a tissue pocket beneath the skin and/or in a cardiac chamber and/or in a coronary vessel such as the coronary sinus.

The MD is particularly preferably an external cardiac pacemaker and/or defibrillator and/or an implantable cardiac pacemaker and/or an implantable cardioverter/defibrillator (ICD) and/or an implantable cardiac resynchronization therapy (CRT) device and/or a neurostimulator and/or a device for monitoring physiological functions such as, but not limited to, a device for monitoring cardiac function.

It is also preferred that the input characteristic of the MD may be modified by means of a switching device having one or more switching elements.

It is further preferred that the switching device has a linear or nonlinear characteristic curve, wherein the characteristic curve properties are implemented by a specialized component and/or material. Use is made, for example, of the characteristic curves for a voltage-controlled capacitor, a voltage-controlled resistor (FET transistor, for example), or a PIN diode. Also used is the characteristic curve for the material composite which implements a GMR sensor. A further assembly for the switching objective referenced here is a multiaxial sensitive Reed switch, for example three Reed switches orthogonally oriented in three spatial directions.

It is also preferred that the switching device is switched using one or more EMI capacitors 310 in series, or that the switching device is switched in parallel using an existing EMI capacitor circuit.

It is also preferred that the input characteristic may be modified using components having voltage-dependent capacitance. In particular, the EMI capacitors themselves may be designed as voltage-controlled capacitors.

It is also preferred that the switching device is designed in such a way that the EMI capacitors are reversed in polarity using a frequency which may be modified and/or predetermined, and/or which is automatically matched to the measured field intensity parameters, the polarity reversals being carried out only for specific field parameters detected by the unit for detecting electromagnetic interference, or carried out continuously.

It is particularly preferred that the switching is carried out using a so-called H-circuit.

It is further preferred that the polarity reversal frequencies of the individual switching elements of the switching device are different and/or time-invariant and/or time-variant.

It is also preferred that the polarity reversal frequency is determined taking into account the polarity of the charge flowing through the electrode line(s).

The charge determination may be based, for example, on the current integral and/or calculated from a voltage measurement of the known capacitance and the electrode impedance as determined by measurement, in each case at the same polarity.

It is also preferred that the switching element of the switching device is a modifiable resistor, modifiable capacitor, semiconductor, or a combination thereof.

The semiconductor switching element is particularly preferably a transistor, thyristor, diode for alternating current (diac), triode for alternating current (triac) switch, and/or a diode.

It is also preferred that the switching of the switching device or the changing of the operating point on the characteristic curve is triggered electrically, optically, acoustically, magnetically, or thermally.

It is also preferred in special cases that the connection of the input lines via the EMI capacitors has to be ensured only when the interference has a given frequency or lies in a given frequency range. In this respect the switching device may be regarded as a frequency-dependent switch, i.e., as a device whose impedance at a given frequency decreases by more than 3 dB only in the surroundings such as, but not limited to, a bandwidth <10 MHz. This may be realized using an LC series circuit.

It is also preferred that the switching device functions depending on the frequency and is designed as an LC series circuit, the resonance of the LC series circuit being settable to the interference frequency to be diverted. For example, the setting may be made by making use of the EMI capacitance, which is present anyway. The resonance is settable to the interference frequency to be diverted, and may, for example, be set by programmed switching of the L and/or C components.

It is further preferred that a communication unit is also present which is designed to establish a unidirectional or bidirectional connection with an MRI device that is present.

It is particularly preferred that the unidirectional or bidirectional connection is established via telemetry and/or RF communication, and/or on the basis of RFID and/or the induction of targeted electromagnetic interference. Also possible are connections based on other, nonwired processes such as, but not limited to, mobile wireless processes, and data transmission standards such as WLAN, Bluetooth, and/or Certified Wireless USB.

It is also particularly preferred that the MRI device is able to trigger and/or control switching of the switching device and/or change the operating point on the characteristic curve of the switching device by means of the communication unit of the MD or IMD.

It is also preferred that the unit for identifying electromagnetic interference for the detection of electromagnetic fields includes at least one of the following sensors or indicators: GMR sensor, MagFET sensor, Hall sensor, electro-optical converter as indicator, monitoring of battery voltages during capacitor charging processes as indicator, detection of RF fields as indicator, detection of magnetic gradient fields as indicator, detection of currents induced by electromagnetic fields as indicator, and detection of specific vibrations, or components designed as sensors for detection of vibrations induced by Lorentz forces, as indicator.

It is further preferred that, in addition to modifying the input characteristic, at least one of the following measures is initiated for detecting electromagnetic interference fields: changing to an MRI safe state, remaining for a prolonged period of time in an MRI safe state or a state that is insensitive to electromagnetic interference fields, synchronization of electrical measurements (impedance measurements, for example) using field intensity minimum values occurring with periodic or pulsed electromagnetic fields, or synchronization of a stimulation using these same minimum values, and emission of electromagnetic pulses for signaling that a medical device, in particular an implant, is present in the electromagnetic field, in particular for signaling to an MRI device, with the possibility of thus transmitting information as well as the interference and displaying same on the MRI screen.

It is further preferred that a position sensor is used for plausibility checking, and a positive MRI identification is made only when the position sensor reports a prone posture and/or another presettable posture.

The position sensor is particularly preferably self-calibrating, the calibration taking place under presettable boundary conditions such as, but not limited to, times and/or heart rates and/or respiratory rate and/or hemodynamic parameters and/or activity (motion sensor).

Also preferred is a method for producing an MRI safe state of an MD by use of one of the MDs.

BRIEF DESCRIPTION OF THE DRAWINGS

Several aspects of the invention are illustrated in FIGS. 1 through 8.

DETAILED DESCRIPTION OF THE INVENTION

Figure 1:
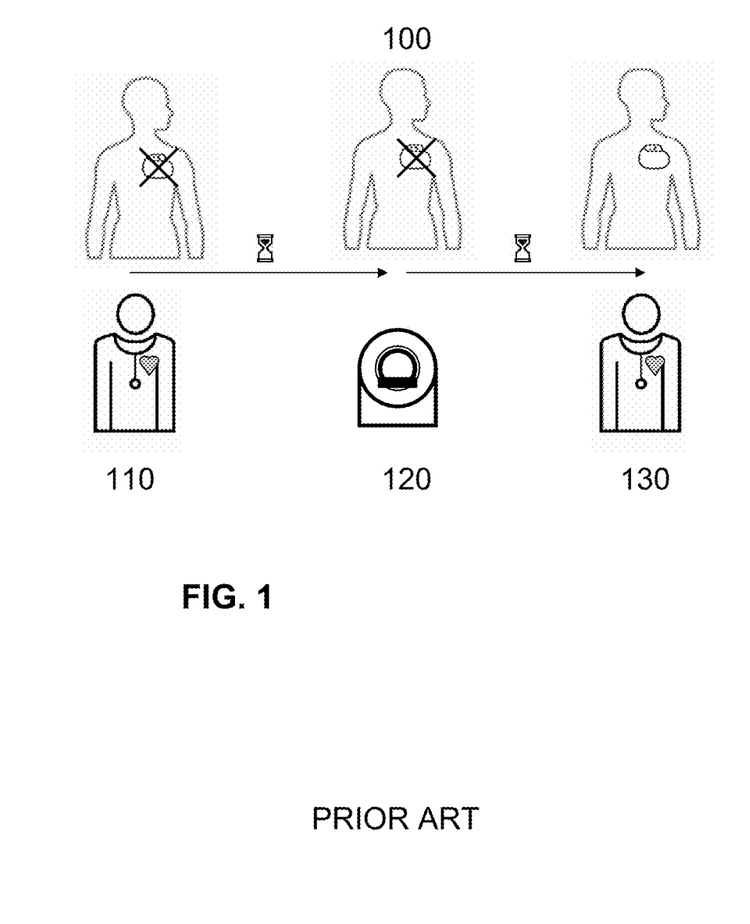
FIG. 1 shows a schematic illustration of the sequence of an MRI test.

FIG. 1 describes the prior art, in which the ICD patient 100 receives follow-up care from a cardiologist before the planned MRT test, and the ICD is switched off 110. After a time delay of hours to days the MRT test is performed by a radiologist 120. After a further delay the patient is once again under the care of the cardiologist 130, and the ICD is switched back on. During the entire time from 110 to 130 the patient is without protection of the implanted defibrillator, and is essentially without rhythm monitoring. This residual risk is accepted in return for the benefits of the MRT test.

Figure 2:
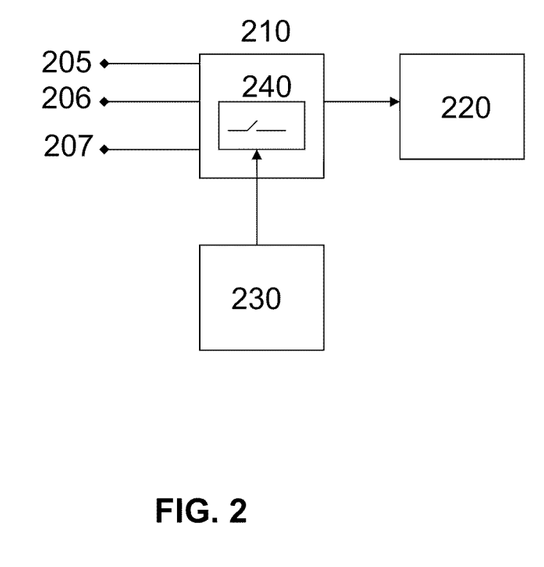
FIG. 2 shows a block diagram of an EMI protective device switched according to the invention.

FIG. 2 shows a block diagram of the approach according to the invention, in which the incoming electrode lines (206 right ventricular, 205 right atrial, and 207 shock line for emitting high-energy pulses) are connected to the input protection circuit 210, and the characteristic of the input protection circuit 210 may be modified by a unit for detecting electromagnetic interference 230. The input characteristics of the electrodes for the electronics system of the MD or IMD together with the switching device 240 are collectively referred to as an input protection circuit 210. The signals from the electrode lines 205, 206, 207 which may be modified or manipulated by the input protection circuit 210 are relayed to the implant electronics system 220, which may include a communications unit for external communications into and out of the IMD, for example to an MRI unit. For the invention it is irrelevant, as is clearly evident to one skilled in the art, whether the implant has one or several electrode lines 205, 206, 207. Variants are also conceivable in which one, several, or all electrodes are designed only as areas on the exterior of the implant.

As a result of the invention, precautions for necessary MRT safety, or for general safety in intense RF fields, are taken only when this boundary condition is present, and in the function mode of the implant, which is necessary the vast majority of the time, the settings may be optimized in favor of the signal quality. The approach according to the invention also takes into consideration that excessively high EMI capacitors 310 increase the hazard potential of stimulation from gradient fields in the MRT.

In general terms, this means that when a strong electromagnetic field is detected, in particular RF fields which occur in the surroundings of MRT scanners which represent a hazard potential for the patient and the implant, the EMI protective circuit of the implant is automatically reconfigured. In the simplest case, for this purpose the EMI capacitor values are increased, or first of all the EMI capacitors 310 are switched on or an existing protective circuit is switched in parallel. To this end their common contact point, for example on the implant housing, may be disconnected by a switch, thus allowing the high-resolution, broadband signal recording, in particular also the impedance determination for a hemodynamic sensor, in everyday operation of the implant. Particularly high EMI capacitors are necessary for minimizing the interactions with RF fields. However, this increases the risk that gradient fields may induce currents, capable of stimulation, which would find a lower-impedance path over the high EMI capacitors. According to the invention this risk is minimized by repetitively changing the polarity of the capacitors, so that during a polarity it is not possible for sufficient charge to flow in one direction to depolarize the cardiac muscle tissue. This allows the requirements for high interference immunity and very high signal recording quality to be combined in an electronic implant. This approach also minimizes the risk of inadvertent, and thus potentially arrhythmogenic, stimulation by gradient fields.

Figure 3:
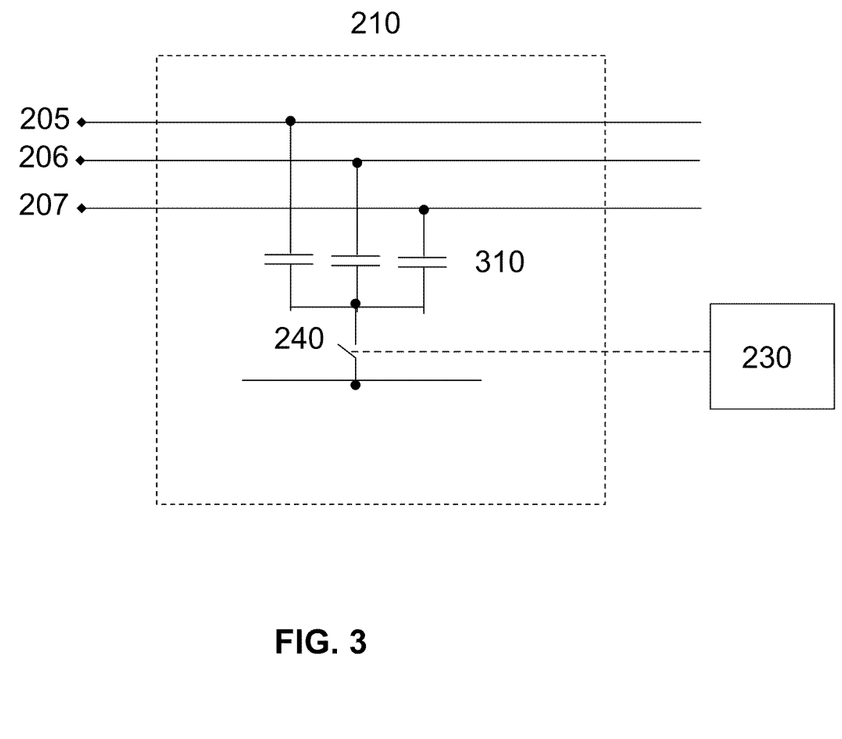
FIG. 3 shows a more detailed block diagram of an EMI protective device switched according to the invention.

In another exemplary embodiment shown in FIG. 3, EMI capacitors 310 are decoupled from the housing by a switching device 240 as a function of the measurements of the unit for detecting electromagnetic interference 230. The EMI capacitors 310 and the switching device 240 are part of the input protective device, and the EMI capacitors 310 are switched via a common switching device 240.

Figure 4:
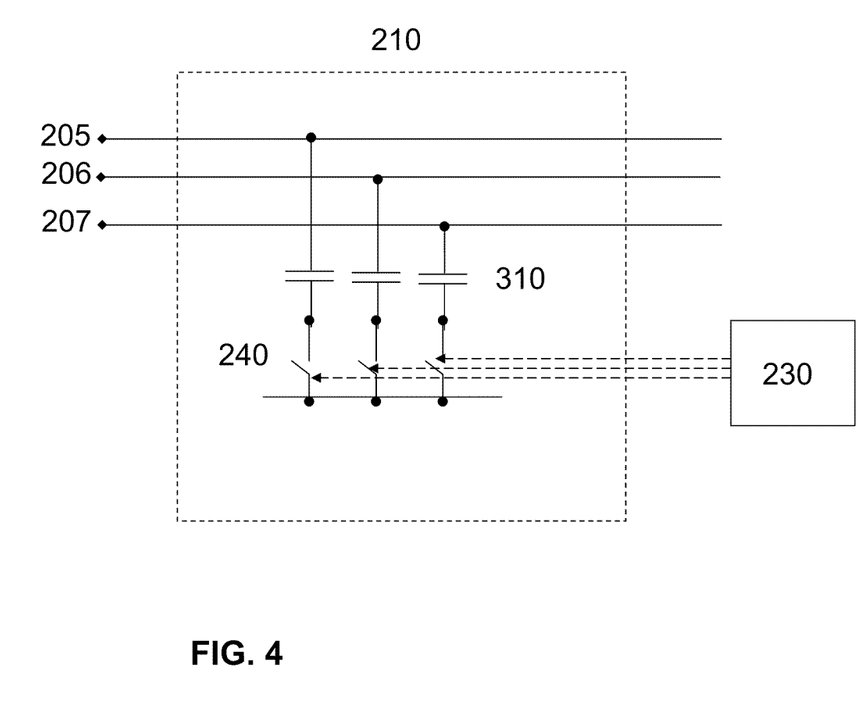
FIG. 4 shows a block diagram of a variant of an EMI protective device switched according to the invention.

The design variant in FIG. 4 has a design analogous to that of FIG. 3, except that each EMI capacitor has its own switching device 240, which in each case may be switched separately from the unit for detecting electromagnetic interference 230.

Figure 5:
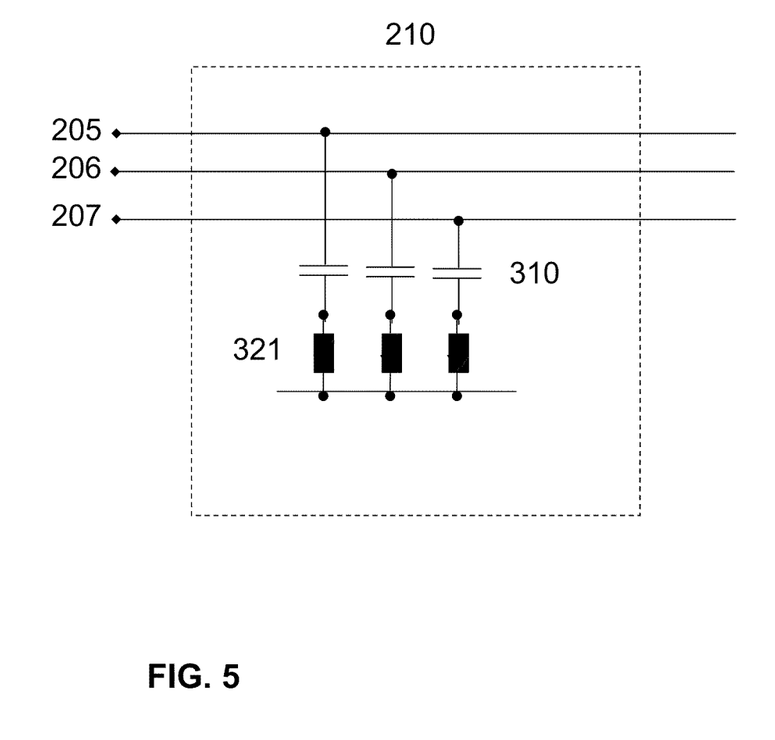
FIG. 5 shows a block diagram of a variant of an EMI protective device switched according to the invention.

In special cases, for the approach according to the invention it is sufficient to ensure the connection of the input lines via the EMI capacitors only when the interference has a given frequency or lies in a given frequency range. In this respect the switching device may be regarded as a frequency-dependent switch, i.e., as a device whose impedance at a given frequency decreases by more than 3 dB only in the surroundings (for example, a bandwidth <10 MHz). This may be realized using an LC series circuit, as shown in FIG. 5. The inductance 321 is matched to the EMI capacitor 320 in such a way that the resonance occurs at the frequency (deviation in terms of the referenced bandwidth) at which the input line is to be switched at the lowest possible impedance from the implant housing. The losses from components L and C are taken into account in their selection so that the quality of the resonant circuit Q is >10.

To allow this approach to be used within the same implant for various interference frequencies, the approach according to the invention provides that the C or L (or both) may be switched over. The switching may occur as a function of the interference field detection unit (which determines the frequency of the interference and selects the matching LC combination). Alternatively, the switching may be performed by the external programming device.

Figure 6:
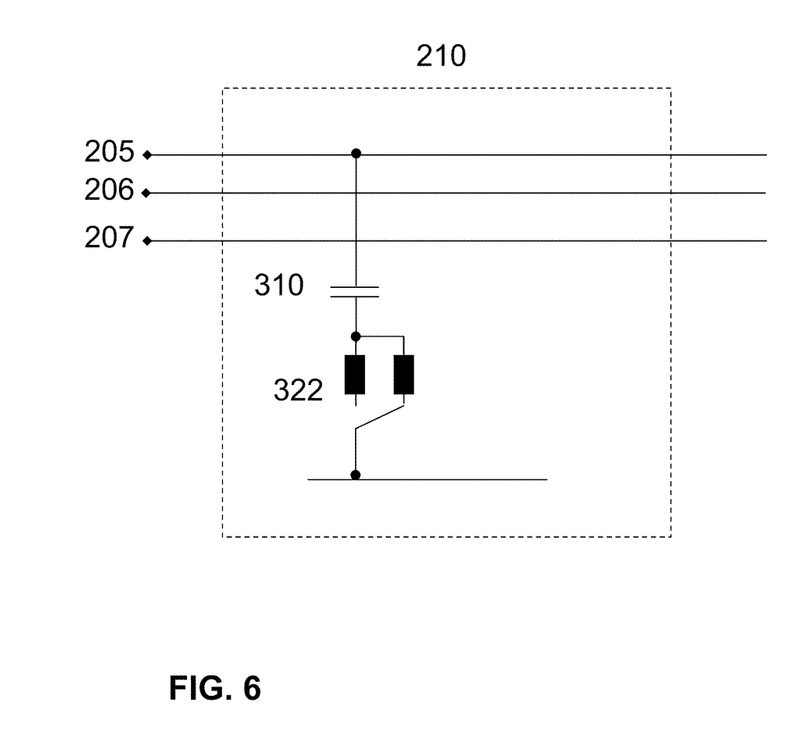
FIG. 6 shows a block diagram of a variant of an EMI protective device switched according to the invention.

FIG. 6 shows only the example of the switchable inductance 322. To adjust (reduce) the quality, the inductance may be shunted via a corresponding resistor. The device is dimensioned (L, C, including the losses thereof, and optionally the shunt resistor) so that during resonance the input lines are thus coupled to the housing at an impedance of <200 ohm (per line).

Figure 7:
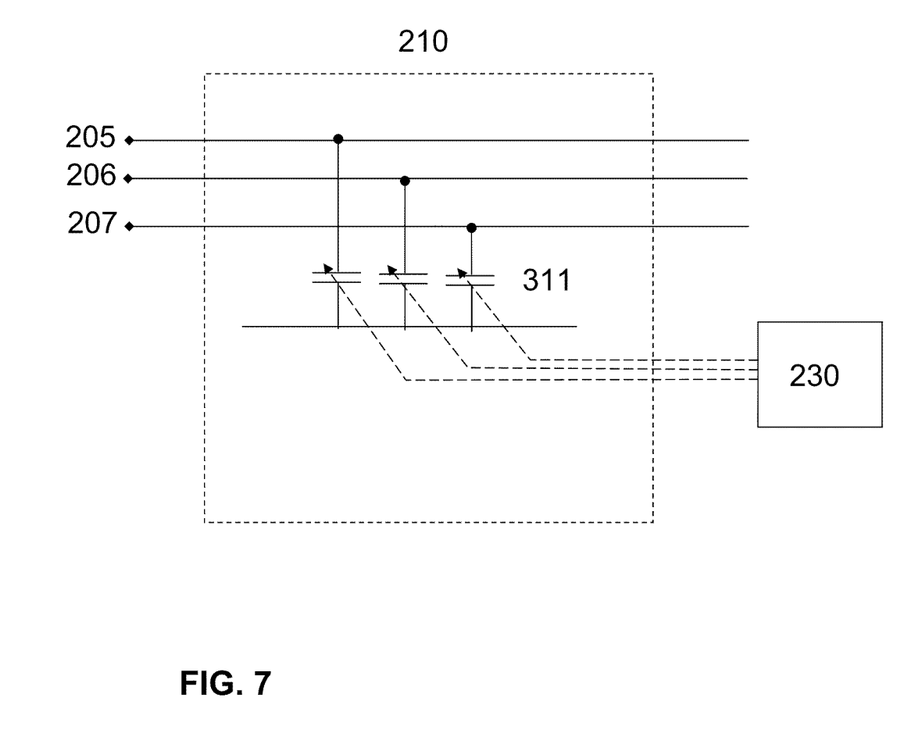
FIG. 7 shows a block diagram of a variant of an EMI protective device switched according to the invention, with controllable capacitors.

FIG. 7 shows an exemplary embodiment in which instead of the EMI capacitors 310 controllable EMI capacitors 311 are used, which in each case are controlled directly by the unit for detecting electromagnetic interference 230, so that a switching device 240 may be dispensed with. The circuit illustrated in FIG. 7 is a so-called H-circuit, which preferably may be used for polarity reversal.

Figure 8:
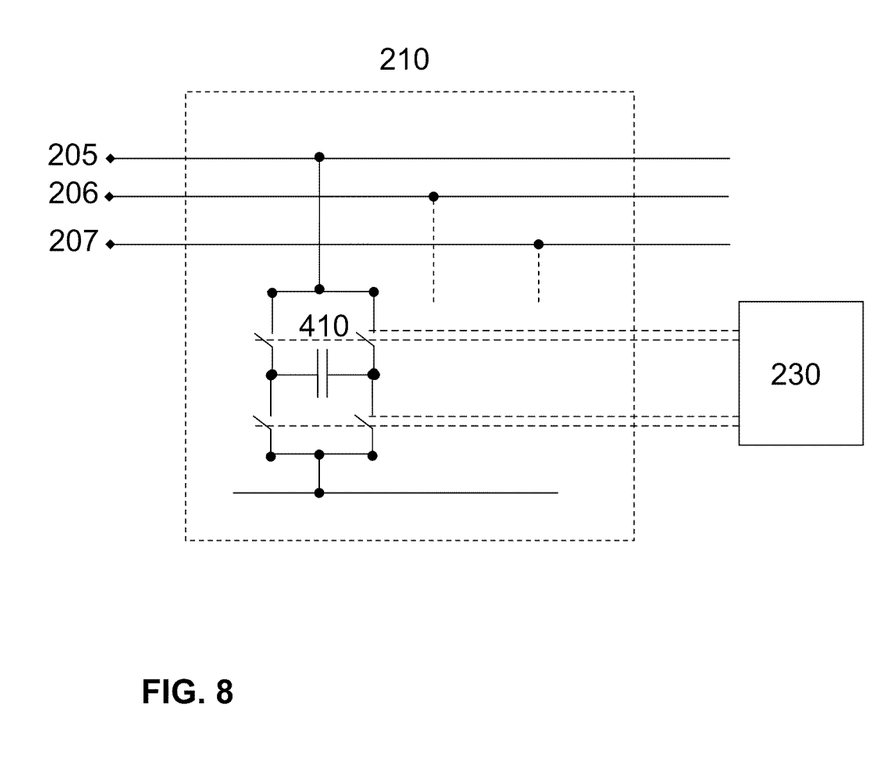
FIG. 8 shows a block diagram of a variant of an EMI protective device switched according to the invention by means of an H-circuit.

FIG. 8 shows an input protection circuit 210 analogous to that in FIG. 3, wherein the switched EMI capacitor 410 is switched by an H-circuit, thus allowing periodic polarity reversal. The H-circuit for the switched EMI capacitor 410 is controlled by the unit for detecting electromagnetic interference 230. Only one switched EMI capacitor 410 in an H-circuit is illustrated in FIG. 8, the dashed lines indicating an analogous design for the other electrode lines 206 and 207. In one variant of this exemplary embodiment, all electrode lines 205, 206, and 207 are connected to an EMI capacitor 410 in an H-circuit.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A medical device comprising:
    a unit configured to detect electromagnetic interference, having at least one sensor and/or indicator for electromagnetic interference fields;
    at least one switching device coupled with said unit configured to detect electromagnetic interference;
    at least one electrode coupled with said at least one switching device;
    at least one control unit coupled with the at least one electrode wherein said at least one control unit is further coupled with said unit configured to detect electromagnetic interference;
    wherein the at least one switching device comprises one or more individual switching elements, and is configured to be switched in series with one or more electromagnetic interference capacitors, or the at least one switching device is configured to be switched in parallel with one or more electromagnetic interference capacitors;
    wherein the at least one switching device comprising one or more individual switching elements is configured so that the electromagnetic interference capacitors are reversed in polarity using one or more frequencies which are modified, and/or predetermined, and/or automatically matched to measured field intensity parameters, wherein a polarity reversal is carried out only for specific field parameters detected by the unit, or wherein a polarity reversal is carried out continuously; and,
    wherein the at least one electrode is configured to contact bodily tissue which enables detection of electromagnetic interference fields by said unit and wherein said at least one switching device is configured to automatically modify an input characteristic of the at least one electrode in such a way that influences of the electromagnetic interference fields to said medical device are minimized.

2. The medical device according to claim 1, wherein the at least one switching device has a linear or nonlinear characteristic curve.

3. The medical device according to claim 2, wherein a switch of the at least one switching device or a change of an operating point on a said characteristic curve is triggered electrically, optically, acoustically, magnetically, or thermally.

4. The medical device according to claim 1, further comprising a communication unit configured to establish a unidirectional or bidirectional connection with a magnetic resonance imaging device.

5. The medical device according to claim 4, wherein the at least one switching device is configured:
    to be triggered and/or have switching controlled by said magnetic resonance imaging device via the communications unit and/or,
    to have an operating point changed on a characteristic curve of the at least one switching device by said magnetic resonance imaging device via the communication unit.

6. The medical device according to claim 1, wherein the medical device is an implantable medical device.

7. The medical device according to claim 1, further comprising components having voltage-dependent capacitance, wherein said components are configured to modify the input characteristic.

8. The medical device according to claim 1, wherein said frequencies used for said polarity reversal are different for individual switching elements of the at least one switching device, and/or time-invariant or time-variant.

9. The medical device according to claim 1, wherein at least one of said one or more frequencies used for said polarity reversal is configured to be determined using a polarity of a charge flowing through an electrode line coupled with said at least one electrode.

10. The medical device according to claim 1, wherein the one or more switching elements comprises is a modifiable resistor, modifiable capacitor, semiconductor, or a combination thereof.

11. The medical device according to claim 1, wherein the at least one switching device functions based on a frequency and is configured as an LC series circuit, wherein a resonance of the LC series circuit is set to an interference frequency to be diverted.

12. The medical device according to claim 1, wherein the unit configured to detect electromagnetic interference includes at least one of the following sensors or indicators:
    GMR sensor,
    MagFET sensor,
    Hall sensor,
    electro-optical converter,
    battery voltage sensor configured to monitor voltage during capacitor charging,
    RF field detector,
    magnetic gradient field detector,
    current detector for currents induced by electromagnetic fields,
    vibration detector, for detection of vibrations induced by Lorentz forces.

13. The medical device according to claim 1, wherein in case of detection of electromagnetic interference fields and in addition to a modification to said input characteristic, said medical device is configured to:
    change to a magnetic resonance imaging safe state,
    remain for a prolonged period of time in a magnetic resonance imaging safe state or a state that is insensitive to electromagnetic interference fields,
    synchronize electrical measurements with field intensity minimum values that occur with periodic or pulsed electromagnetic fields, or synchronize a stimulation with said field intensity minimum values, and
    emit electromagnetic pulses to signal that the implantable medical device is present in an electromagnetic field, and to further signal to a magnetic resonance imaging device and transmit information regarding interference for display on a magnetic resonance imaging screen.

* * * * *